United States Patent
Kerrigan et al.

(10) Patent No.: US 10,051,831 B2
(45) Date of Patent: Aug. 21, 2018

(54) **METHODS FOR PRODUCTION OF SPORELESS *AGARICUS BISPORUS* MUSHROOMS**

(75) Inventors: Richard W. Kerrigan, Kittanning, PA (US); Anthony J. Velcko, Jr., Ford City, PA (US); Mark C. Spear, Kittanning, PA (US); Mark P. Wach, Allison Park, PA (US)

(73) Assignee: SYLVAN AMERICA, INC., Kittanning, PA (US)

( * ) Notice: Subject to any disclaimer, the term of this patent is extended or adjusted under 35 U.S.C. 154(b) by 540 days.

(21) Appl. No.: 13/810,552

(22) PCT Filed: Jul. 16, 2010

(86) PCT No.: PCT/US2010/042289
§ 371 (c)(1),
(2), (4) Date: Feb. 15, 2013

(87) PCT Pub. No.: WO2012/008969
PCT Pub. Date: Jan. 19, 2012

(65) Prior Publication Data
US 2013/0139275 A1    May 30, 2013

(51) Int. Cl.
*A01H 1/02*    (2006.01)
*A01H 15/00*   (2006.01)
*A01G 18/00*   (2018.01)

(52) U.S. Cl.
CPC ............. *A01H 15/00* (2013.01); *A01G 18/00* (2018.02); *A01H 1/02* (2013.01)

(58) Field of Classification Search
None
See application file for complete search history.

(56) References Cited

U.S. PATENT DOCUMENTS

| 5,304,721 A | 4/1994 | Kerrigan et al. | |
| 5,684,228 A * | 11/1997 | Kerrigan | A01H 15/00 435/6.13 |
| 6,521,817 B2 * | 2/2003 | Callac | A01H 15/00 47/1.1 |

FOREIGN PATENT DOCUMENTS

| WO | WO0112850 | 2/2001 | |
| WO | WO 0112850 A1 * | 2/2001 | ............... A01G 1/04 |

OTHER PUBLICATIONS

Agaricus bisporus. In Science and Cultivation of Edible Fungi. vol. 1. Ed. L.J.L.D. Van Griensven.Proceedings of the 15th international congress of the science and cultivation of edible fungi. Maastricht, Netherlands. May 15-19, 2000. pp. 183-190.*

Miller et al (Inheritance of Sporophore Color and "Wild" Morphology in *Agaricus bisporus*. Mushroom Science IX (Part I). Proceedings of the Ninth International Scientific Congress on the Cultivation of Edible Fungi, Tokyo, p. 39-46, 1974).*

Fritsche (Breeding *Agaricus bisporus* at the mushroom experimental station, Horst. Mushroom J. 122:49-53, 1983).*

* cited by examiner

*Primary Examiner* — Medina A Ibrahim
*Assistant Examiner* — Wayne Zhong
(74) *Attorney, Agent, or Firm* — Renner Kenner Greive Bobak Taylor & Weber

(57) ABSTRACT

Methods of producing hybrid *Agaricus bisporus* mushrooms strains derived or descended from at least one wild mushroom strain and having the specified traits of either greatly diminished sporulation or an absence of sporulation, and of obtaining postmeiotic offspring of nonsporlating basidiomycete fungi including *Agaricus bisporus*, are disclosed.

3 Claims, 2 Drawing Sheets

METHODS FOR PRODUCTION OF SPORELESS *AGARICUS BISPORUS* MUSHROOMS

RELATED APPLICATIONS

None.

TECHNICAL FIELD

This invention relates to a method for production of mushrooms. More particularly, this invention relates to a method of production of one or more strains of the cultivated mushroom fungus *Agaricus bisporus* (Lange) Imbach, that produce mushrooms that either express, or possess in a latent state, one or more traits selected from the group consisting of non-sporulation, reduced sporulation, incomplete development of spores, incomplete release of spores, and paler lamellae.

BACKGROUND OF THE INVENTION

The basidiomycete fungus *Agaricus bisporus* (Lange) Imbach var. *bisporus* produces a mushroom (technically, an agaric basidiome with a pileus, stipe, veil, and lamellae). This *Agaricus bisporus* "button mushroom" or "portabella mushroom" is a widely and extensively cultivated species of mushroom. Globally, the annual crop has a value of several billion dollars. The mushrooms are grown commercially on specially-prepared compost in enclosed, environmentally controlled spaces. During maturation, the mushroom primordia form and enlarge on a non-nutritive layer called "casing soil" that is applied to cover the compost. The mushrooms' anatomical structures undergo a developmental progression that, if not interrupted, causes (1) the velar layer covering the lamellae (='gills') to stretch and rupture, (2) the lamellae to be exposed to ambient atmosphere, and also to begin to develop deeper and/or darker coloration, (3) the basidial cells lining the lamellae to undergo nuclear fusion (=karyogamy) followed by meiosis, (4) sterigmata (narrow sporogenic structures) and spore-primordia to appear and enlarge on the distal apex of the basidia, (5) one or more haploid postmeiotic nuclei to migrate into each 'basidiospore', (6) the spores to develop a dark brown wall pigmentation, and (7) mature spores to be forcibly discharged from the sterigmata and to become airborne. The development and release of fungal spores jointly comprise and define sporulation.

Traditional commercially-used strains of *Agaricus bisporus* were originally taken directly from naturally occurring mushrooms or from found 'wild' composts in which mushroom mycelium was observed. Some of these older strains are still present in culture collections and at least one such line, which produces brown-capped mushrooms, is still in commercial use. Since the 1970's, a number of laboratories have developed techniques for making fusions between two different strains (equivalent terms are stocks, lines, commercial varieties, etc.) to produce novel 'hybrid' strains incorporating haploid nuclei from the two different parent strains. Most often, but not universally, the term 'strain' is applied to heterokaryotic cultures incorporating two complementary haploid nuclei in a common cytoplasm. A more inclusive general term, culture, includes not only heterokaryotic cultures, but also haploid, homokaryotic cultures, aneuploid cultures, etc.

The *Agaricus bisporus* mushroom species utilizes two complementary life-cycles that operate concurrently, through basidia and basidiospores (=spores), in each mushroom. In one life-cycle, some spores receive two sexually complementary, postmeiotic haploid nuclei, and these 'heterokaryotic' spores can carry out the complete life-cycle from a single germinating spore; however they can only fuse with other spore-cultures poorly. This is an inbreeding system called "pseudohomothallism", "secondary homothallism", or "intramixis", and such spores can be thought of as colonizers. In the other life-cycle, some spores receive only one post-meiotic haploid nucleus, and while such "homokaryotic" spores cannot complete the life-cycle alone, they have the general ability to fuse with and combine genetic material with many other cultures. This is an outbreeding system called "heterothallism" or "heteromixis", and such spores can be thought of as crossbreeders. After fusion by, for example, two compatible homokaryotic spore-cultures, a heterokaryotic culture incorporating both haploid nuclei and capable of completing the life cycle may result. Less often, there are also produced, in low numbers, spores that may receive two sexually incompatible (or second-division "sister") post-meiotic haploid nuclei, as taught by Kerrigan et al. Genetics 133:225-236 (1993); these function as homokaryons but are genetically more heterogeneous. Other rare classes of spores include aneuploid spores and spores sufficiently different, cytogenetically, from the ordinary $n=1.0$ or $n+n=2.0$ chromosomal complement states, to resist easy classification; deletion and truncation of chromosomes can produce this type of nucleus and spore. However, any viable spore-culture has at least some chance of participation in a fusion event with another culture, which will lead to a novel culture and genotype.

Although spores, some of which germinate to produce the haploid (n) homokaryons desired for hybridization, are most often used as the source of cultures used to construct novel hybrid strains, other sources of homokaryons can be obtained using methods that induce the repartitioning of cellular contents including nuclei; specific techniques include subdividing heterokaryotic culture mycelia (e.g. mechanical reduction methods, including but not limited to, microsurgery or laser surgery to sever hyphal tips or fragment mycelia), regenerating protoplasts from heterokaryotic cultures, etc.

A typical defined fusion arises from the anastomosis plus plasmoogamy of two compatible haploid, homokaryotic cultures, and is achieved in the laboratory by placing ("pairing") the two cultures in close proximity on a suitable sterile culture medium, and facilitating anastomosis (=hyphal fusion creating a continuous opening through the hyphal cell wall and the plasma membrane) and plasmogamy (=cytoplasmic mixing). Several other combinations of culture types can also result in fusion processes leading to novel hybrid strains, although such methods generally have a lower probability of success and/or result in one or more undefined hybrid heterokaryotic strains. These methods include pairing a heterokaryon culture with a homokaryon culture, pairing two heterokaryon cultures, pairing cultures at least one of which has at least one nucleus which is either aneuploid or is karyotypically ambiguous or indeterminate (i.e., with respect to ploidy), and preparing undefined mixtures of spores, or spores and mycelium together. All of these cases require microbiological methods that are carried out in the laboratory by the experimenter, using axenic manipulation of pure culture materials on sterile culture media and enclosures, to enable anastomosis and plasmogamy to occur.

Any method, including but not limited to those described above, that allows for a reassociation of genetic material from more than one culture and/or spore, and results in a heterokaryon with a novel hybrid (bi-parental) genotype, is capable of producing an equivalent result. The microbiological methods used to obtain, maintain, and transfer cultures including homokaryons, and which enable fusion via anastomosis and plasmogamy between cultures of basidiomycete fungi, will be referred to herein as "hybridization". By "parent", a heterokaryotic strain is meant. However, most often culture fusions are attempted between two haploid homokaryons. Homokaryotic cultures are clonally propagated, and can live and grow indefinitely, but biologically they are the functional equivalent of gametes such as sperm or eggs. It is incorrect to also call homokaryons simply "parents", and so to make the distinction clear, they will be referred to herein as "homokaryon-parents" as set forth in the definitions below.

Naturally occurring "sporeless" mutations are believed to be rare. A small number of mutations negatively affecting sporulation in some basidiomycete fungi are known. This is not unexpected, given that without sporulation, reproduction of the afflicted individual is prevented. Genetic material from such an individual, including any that determines the trait of sporelessness, will not be represented in the next generation of offspring, and thus such genetic determinants of sporelessness, when they arise spontaneously, are likely to decline in frequency in natural populations. In other words, natural selection against sporelessness tends to reduce the frequency of sporeless genetic determinants (i.e., genetic material determining a trait, for example alleles at a genetic locus) in nature. However, if such a hypothetical mutant allele causing sporelessness has a recessive genetic behavior, and is paired with a functional dominant allele in a heterokaryotic (n+n) strain, then sporulation may occur and the 'masked' mutant allele can be transmitted to future generations, and may be maintained in the population except when paired (in a heterokaryotic individual) with another recessive allele for sporelessness. It is further taught, as in Zolan et al., Mol. Cell. Biol. 6: 195-200 (1986), that in some cases "those few . . . spores that are produced are never more than about 1% as viable as the more numerous spores from wild-type strains".

A small number of "sporeless" basidiomycete strains are known in the art to produce basidiomata (e.g. mushrooms) with only a small number of spores. However, none of these known strains belong to the species *Agaricus bisporus*. For example, Okuda et al., Genome 52(5): 438-446 (2009), teach a "sporeless mutant strain . . . of [*Pleurotus*] *pulmonarius* . . . produces an extremely small number of spores". In the absence of a precise universal definition of "sporelessness" and for purposes of this invention, the trait of "sporelessness," meaning the "sporeless" condition or phenotype, includes the specific traits of non-sporulation, reduced sporulation, incomplete development of spores, incomplete release of spores, and/or paler lamellae as are further defined below.

An example of a naturally occurring sporeless mutation is known in the basidiomycete fungus *Pleurotus ostreatus* as set forth in Eger et al., U.S. Pat. No. 4,242,832. That patent teaches a particular process for producing non-recombined (non-post-meiotic) homokaryons (called "monokaryons", a synonym, in that document) from vegetative heterokaryotic mycelia of basidiomycetes. A sporeless strain designated "42×11" was obtained via inbreeding by fusing two homokaryotic (haploid) single-spore isolates (SSIs) from a single commercial *Pleurotus* mushroom strain. It is interpreted that a recessive genetic determinant for a sporeless trait was inherited by both of the haploid (n), homokaryotic SSI offspring, and when these two offspring were mated, the resulting inbred heterokaryotic (n+n) strain had a doubly recessive genotype for the postulated gene determining sporelessness, and the sporeless trait was consequently expressed and observed in the phenotype of mushrooms formed by the newly created heterokaryotic strain. A drawback of this method is that such offspring share a single common parent and will be inbred (and thus not "hybrid", in the sense of having two different parents), and may, for example, be highly likely to be homozygous for deleterious recessive alleles that could negatively affect any important trait of the strain.

More generally, though, such mutations are obtained by mutagenic processes. This was done on *Coprinopsis cinereus* as taught by Zolan et al., Methods Mol. Biol. 558: 115-27, (2009) and references cited therein. The resulting non-sporulating mutants have been studied by different laboratories, and several different kinds of mutations have been found. In her 1986 article, Zolan et al. wrote that "There are therefore many mutations that could lead to . . . lack of spore formation . . . " including some that would affect meiosis, and some that would not. One drawback of artificial mutagenesis is that many random mutations are created, rather than a single desired mutation, and the resulting mutagenized strains often have multiple genetic defects, and are unsuitable for purposes other than research.

Mikosh et al., WIPO Publication No. WO01/12850 A1 teach a method of "using a nucleic acid molecule or fragment thereof" for marking alleles of genes in basidiomycete fungi. These 'Marker Assisted Selection' methods (=MAS) were and are well-known methods in the art; and the application was abandoned. What Mikosh et al. incidentally demonstrated, using MAS, was one marker that appeared to be linked to one mutation for sporelessness in the fungus *Pleurotus ostreatus*. Subsequently, also using genetic markers, the Okuda et al. 2009 article proposed a chromosomal map location for an unspecified 'sporeless' mutation in the related species *Pleurotus pulmonarius*. Notably, the method of the present invention does not use or require any nucleic acid molecule or fragment thereof, nor any other marker or MAS technique, to mark alleles of any gene hypothetically associated with the production of a sporeless phenotype in mushrooms of *Agaricus*.

Mikosh et al. (2001) further teach, in an entirely imaginary exercise, that their invention " . . . provides an essentially spore-less mushroom obtainable by a method according to the invention, for example . . . obtained from . . . cultures of basidiomycetes such as . . . *Agaricus bisporus* . . . " However, their claimed invention actually required enabling sporeless (either expressed or latent) biological starting material that would necessarily have to have contributed the actual trait for sporelessness. Because no genetic material of *Agaricus bisporus* capable of determining a sporeless trait in that species was known to Mikosh et al., their invention was not in fact able to provide the sporeless *Agaricus bisporus* as alleged, and their statement is believed to be a conjecture. It is in fact the invention of the present application that is uniquely and for the first time able to provide a macro-anatomically normal, sporeless *Agaricus bisporus* mushroom. Further, as noted, the method of our invention does not rely upon MAS methods to accomplish its object.

Mikosh et al. further imagine the possibility of using 'genetic engineering' or DNA-mediated transformational methods to silence or 'knock out' a gene required for sporulation of basidiomycete fungi. Such future developments are trivially easy for practitioners of the art to imagine, but were never accomplished by Mikosh et al. or, to the Applicants' knowledge, by anyone else. Notably, the method of the present invention does not use genetic engineering methods at all, and explicitly not to silence or 'knock out' a gene required for sporulation.

Based on published experiments with *Coprinopsis cinereus* by Zolan et al. and others, documenting the complexity of the meiotic and sporogenic processes, the number of possible genetic defects that can interrupt the development and release of mature, typical, viable spores, and the way that those often unidentified genes interact with the rest of the organism's genotype, there is an expectation of diversity in both the nature and the degree of "sporeless" phenotypes that may be discovered. Per Mikosh et al. (2001) and Okuda et al. (2009), a few spores might be produced in sporeless strains of *Pleurotus*. In *Coprinopsis*, non-viable spores may be produced (Zolan et al. 1986). As explained below, this condition would also be of potential value as it would still be expected to interdict the spread of mushroom viruses by airborne spores, which are believed to be infective only if viable.

The possibility can be anticipated that tiny, aborted spores, or immature unpigmented spores, might be produced. In another instance, mature spores might be developed but not released due to a defect in the spore-release mechanism. The present invention defines 'incomplete development of spores' below to include the above conditions and any others that inhibit the production and/or release of mature, typical, viable spores from otherwise typical mushrooms regardless of the quantity of spores.

In the published literature on *Agaricus*, there are believed to be only a few articles that might appear to have even a remote relationship to the present invention. In fact, these articles describe a fundamentally different phenomenon relating to mutations that produce 'anatomical monstrosities' that do not have the familiar anatomy of typical, normal mushrooms. Fritsche, Mush. Sci. 6: 27-47 (1967) described studies on a series of spontaneous mutations in a single *Agaricus bisporus* culture and a series of its subcultures. In the mutant basidiomata (which were not characteristically (macroanatomically) "agaric" mushrooms in form) the development of entire anatomical structures was prevented. In the first mutation in the sequence, an irregular quasi-mushroom-like structure lacking both lamellae and a stipe (stem) was produced. After a second mutation, these stipeless, nonlamellate bodies became regular in form, somewhat like hens' eggs. Two subsequent mutations led to the production of amorphous masses of undifferentiated tissue not at all resembling mushrooms. Other articles, for example, Umar et al., p. 563-570. In T. J. Elliott [ed.], Science and cultivation of edible fungi, Balkema, Rotterdam (1995), teach similar or other types of irregular 'monstrosities' that might hypothetically arise from what may be a same or similar, or a distinct, mutation. In severe cases the monstrosities that are formed lack many anatomical features, among which lamellae may be absent. Technically, basidiomata lacking lamellae and basidia may incidentally be sporeless, but are not macroanatomically normal as defined herein. In contrast, the commercially desired sporeless mushroom is macroanatomically normal, and looks completely familiar to the consumer.

In the absence of meiosis, no genetic recombination will occur in a sporeless strain, and without spores, there is no inherent way for sexual offspring to be produced. Both of these behaviors present obstacles to the creation of sporeless strains, and the lack of available desirable native genetic material causing sporelessness without incurring the deleterious consequences of random mutagenesis to the strain is yet another impediment. Prior to the development of the present invention, no evidence for the existence of the sporeless trait or of natural or artificial genetic determinants for sporelessness in *Agaricus* were known.

Sporulation of commercially cropped mushrooms is undesirable for several reasons. Spores from mushrooms infected with dsRNA viruses are known to incorporate virus copies and airborne spores can spread the infection within and between facilities, making disease control very difficult. Virus diseases of *Agaricus* mushroom crops are known to reduce productivity, delay crops, and alter the appearance of product in ways that reduce or eliminate its commercial value. At higher concentrations of mushroom and other fungal spores, such as can occur in enclosed mushroom production facilities, there is a risk of an allergic response and/or respiratory distress in humans. In *Agaricus*, the spores are a dark 'chocolate brown' color (approximately 187A in the RHS color chart system), and dark spores on the surfaces of the lamellae darken the lamellae as seen and contribute to a visual impression of age (overmaturity or lack of freshness) in fresh mushroom product. For specific products with opened mushroom-caps, such as 'flats' or 'portabellas', the release of spores after harvest and their deposition on other harvested product or packaging can ruin the appearance and commercial value of fresh ('raw' or unprocessed) product. Dark spores on lamellae also cause a darkening of moist food dishes incorporating mature mushrooms, often detracting from the appearance of the finished dish.

To counteract many of these problems, mushrooms have traditionally been picked when immature, as 'buttons', 'cups' or 'closed caps'. However, the earlier a mushroom is harvested, the less it weighs, and so early harvesting strategies can carry a potential yield penalty and loss of profit. In recent years a market segment for open mushrooms has expanded, in part because mature mushrooms may be perceived to be more flavorful. Commercial production of open mushrooms potentially incorporates all of the negative hygienic and other consequences noted hereinabove.

Mushrooms with lamellae that are paler at any stage of development, relative to and in comparison to typical commercial strains, are highly desirable. Paleness may be obvious or may be established objectively and quantitatively as described herein.

Accordingly, there is a need for new mushroom strain capable of producing visually (macroanatomically) typical mushrooms that have a greatly reduced, or no, capacity for sporulation, by which is meant the production and release of mature, typical, viable spores, as well as acceptable productivity, vigor, timing, and appearance. There is also a need for a method to enable the development of sporeless *Agaricus* strains, by providing strains with native genetic materials that (1) confer the trait of sporelessness upon strains, that further (2) do not interfere with meiotic recombination, and yet further that (3) via suitable methods can provide recombinant offspring through multiple generations of hybridization. There is yet another need, for a method of obtaining postmeiotic offspring in the absence of sporulation.

SUMMARY OF THE INVENTION

For purposes of the present invention, the following terms have been defined.

By the term "culture," it is meant a product of the cultivation of a living microorganmism in prepared nutrient media. Such a microorgamism may include, for example, fungal mycelium including mycelia that are heterokaryotic, haploid, homokaryotic, and aneuploid.

By the term "strain," it is meant heterokaryotic cultures that have two complementary haploid nuclei (i.e. cultures with an n+n nuclear chromosomal complement as the cytogenetic status) in a common cytoplasm; "heterokaryon" is an equivalent term.

By the term "homokaryon," it is meant a haploid culture having a single (n) nuclear chromosomal complement.

By the term "parent," it is meant a heterokaryotic strain that contributes one of the two nuclei that becomes incorporated into a hybrid heterokaryotic offspring.

By the term "homokaryon-parent," it is meant a haploid, homokaryotic culture (=homokaryon) derived from a heterokaryotic parent strain and which can function as a donor of one of the two haploid nuclei incorporated in a hybrid heterokaryotic offspring.

By the term "wild strain" or "wild culture" it is meant a strain or culture obtained from nature.

By the term "wild germ plasm," it is meant the hereditary material or DNA of naturally occurring strains and cultures, and also of strains and cultures isolated from naturally occurring sources, and also such material that may have been transmitted to descendents, including hybrid offspring, over any number of generations.

By the term "pedigree," it is meant an inclusive grouping or 'family' that is genealogically related, originates with the parents of a first hybrid strain, and includes all members of all generations descended from that first hybrid strain.

By the term "descended," it is meant that a more recent hybrid strain is genealogically related in a direct lineage to a series of pre-existing strains including, e.g., parents and grandparents, by one or more generations of hybridization.

By the term "derived," it is meant that a strain has been obtained from a pre-existing strain by methods of manipulation or selection not involving hybridization, but instead including but not limited to spore selection, somatic selection, mutagenesis, DNA-mediated transformation and genetic engineering.

By the term "sporulation," it is meant the development and release of fungal spores.

By the term "sporelessness," it is meant a sporeless phenotype, including any of the specific traits of non-sporulation, reduced sporulation, incomplete development of spores, incomplete release of spores, and/or paler lamellae, as further described above and defined herein.

By the term "non-sporulating" or "non-sporulation," it is meant a trait or condition wherein there is a reduction of 99% or more in the number of mature, typical, viable spores released, relative to that of a commercial control strain, namely Sylvan SB-65, which control strain is currently deposited in the Agricultural Research Service Culture Collection (NRRL) Patent Depository collection under the Budapest Treaty in Peoria, Ill., USA, and has been assigned the deposit number NRRL 50409 This strain was deposited on Jul. 13, 2010. The deposited strain will be maintained in the depository for at least 30 years from the filing date of the application, or for the effective life of the patent, whichever is longer, and will be replaced if necessary. This strain will be irrevocably and without restriction or condition released to the public upon the issuance of a patent.

By the term "reduced sporulation," it is meant a trait or condition wherein there is a reduction of between 50% and 99% in the number of mature, typical, viable spores released, relative to that of the commercial control strain Sylvan SB-65, when the mushrooms being compared are of substantially the same size, and at substantially the same stage of expansion and maturation.

By the term "incomplete development of spores" it is meant the condition or conditions that inhibit the production and/or release of mature, typical, viable spores from otherwise typical mushrooms regardless of the quantity of spores, when the mushrooms being compared are of substantially the same size and at substantially the same stage of expansion and maturation.

By the term, "incomplete release of spores" it is meant the condition wherein spores are not forcibly discharged from the basidia.

By the term "paler lamellae" it is meant that the lamellae are observably or measurably less dark or less pigmented relative to the control strain Sylvan Sylvan SB-65, when the mushrooms being compared are at substantially the same stage of expansion and maturation. Actual measurability of the paleness is discussed hereinbelow.

By the term "macroanatomically normal," it is meant that, to the naked eye, all of the familiar anatomical elements of an ordinary mushroom, including lamellae and a stipe, are set forth in their normal form, place and proportion. Such a mushroom will look completely familiar to a consumer.

The advantages of the present invention over existing prior art relating to *Agaricus bisporus* mushrooms and known mutants, which shall become apparent from the description which follows, are accomplished by the invention as hereinafter described and claimed. One aspect of the present invention is to provide a macro-anatomically normal, sporeless *Agaricus bisporus* mushroom. Another aspect of the present invention is to provide a method for the production of one or more strains of the cultivated mushroom fungus *Agaricus bisporus* that produce mushrooms that are sporeless. The mushrooms either express, or possess in a latent state, one or more traits selected from the group consisting of non-sporulation, reduced sporulation, incomplete development of spores, incomplete release of spores, and paler lamellae, as defined hereinabove. In at least one embodiment, the sporeless mushrooms are macroanatomically normal. In at least another embodiment, the method of the present invention does not use or require any nucleic acid molecule or fragment thereof, nor any other marker or MAS technique, to mark alleles of any gene hypothetically associated with the production of a sporeless phenotype in mushrooms of *Agaricus*.

It will be appreciated that at least some of these traits are based upon a comparison with the commercial control strain Sylvan SB-65. To conduct a proper comparison between two strains and to insure consistency in the comparison, mushrooms of substantially the same size and substantially the same developmental stage of maturity must be evaluated using the same methodology. One of skill in the art should readily be able to determine whether such a strain is "non-sporulating," without undue experimentation in the art, and most often, will be reasonably able to evaluate the "sporulation" or "non-sporulation" of the mushroom either with a simple microscopic examination of the lamellae, or with the naked eye by, for example, suspending caps of the mushrooms over white paper in still air, and making a visual observation of any spore deposit, or the absence thereof, on the paper after 24, or more, hours of exposure. Furthermore, if a precise quantitative method is required, then identical targets such as glass coverslips can be placed beneath the mushroom caps for a standard interval of 24 hours or greater, the spores can be suspended in a standard volume of water, one or more dilution steps can be carried out, and the spore concentration determined using any one of a variety of available cell-counting devices. In the comparison of counted data, if the number of spores counted in a unit volume of the spore suspension from the control mushroom is 100 or more times greater than the count from an equal volume of the suspension from the mushroom being evaluated, then the latter mushroom is non-sporulating.

The same comparison methods can determine the conditions that are herein defined quantitatively as reduced sporulation and incomplete release of spores. For example, in the comparison of counted data, if the number of spores counted in a unit volume of the spore suspension from the control mushroom is 50 or more times greater than, but less than 100 time greater than the count from an equal volume of the suspension from the mushroom being evaluated, then the latter mushroom is said to express the reduced sporulation trait, Incomplete development of spores is easily observed using a compound microscope to examine samples of lamellae, whereby spores can be measured and photographed, and their shapes and pigmentation can be documented. Viability of spores can be determined by transferring a known quantity of spores suspended in dilution in water onto petri dishes containing a medium such as PDA, and counting the number of colonies arising from germinated spores after 14 or 21 days.

The condition or trait of paler lamellae may be established objectively and quantitatively. For example, given samples of mushrooms of comparable sizes and ages, and using a device such as a Minolta Chroma Meter, reporting objective color measurements using a system such as the L-a-b color space, used to measure the color of lamellae from at least ten mushrooms for each treatment including the control, and, using a suitable test such as a t-test, reporting a statistically significant difference on a relevant scale, such as the L scale, such that the set of control measurements has, for example, a lower L value, at a significance level of $p<=0.05$, can thereby determine that the lamellae of the mushroom being evaluated are paler than those of the control mushroom.

Further, as noted above, the method of our invention does not rely upon Marker Assisted Selection methods to accomplish its object. By identifying and incorporating wild germ plasm capable of transmitting the trait, and putatively carrying genetic determinants for non-sporulation, into novel breeding pedigrees, a method for creating hybrid mushroom strains of *Agaricus* that do not sporulate has been found, including strains with other commercially acceptable and desirable attributes. By employing a further method of obtaining postmeiotic offspring of sporeless mushroom strains, sporeless pedigrees can be constructed that can be recombined and improved over multiple generations in the absence of spores.

It is still another aspect of the invention to provide a method for obtaining sporeless strains of *Agaricus bisporus* mushrooms with acceptable or even improved attributes required for commercial use. Specifically it is an aspect of the invention to provide cultures capable of producing mushrooms with characteristics and appearances suitable for use in diverse segments of the commercial edible mushroom product market, including closed and open mushrooms, fresh and processed mushrooms, whole mushrooms and parts (caps, slices) of mushrooms, gilled and gill-less mushrooms, small, medium and large mushrooms, and white, light brown and dark brown mushrooms, among other variable attributes, as required by the market.

One or more of these and other aspects of the invention have been accomplished by providing a method of producing hybrid mushroom strains comprising the step of enabling fusion via anastomosis and plasmogamy between a first culture of *Agaricus bisporus* selected from the group consisting of (a) a wild culture capable of transmitting to offspring at least one trait selected from the group consisting of non-sporulation, reduced sporulation, incomplete development of spores, incomplete release of spores and paler lamellae, (b) a culture derived therefrom, and (c) a culture descended therefrom, and at least a second culture. The method may further include the step of induced cellular repartitioning of contents of postmeiotic cells from a non-sporulating culture to derive any culture used to enable fusion. In one embodiment and for either or both of the steps above, the first culture of *Agaricus bisporus* may be selected from the group consisting of a wild *Agaricus bisporus* culture of the tetrasporic variety *burnettii*, a culture derived therefrom, and a culture descended therefrom. In another embodiment, and for either or both of the steps above, the first culture may be selected from the group consisting of a wild *Agaricus bisporus* culture JB-2, a wild *Agaricus bisporus* culture JB-28, a culture derived from JB-2 or JB-28, and a culture descended from JB-2 or JB-28. In another embodiment, and according to any of the embodiments above, the at least one trait is phenotypically expressed in a member of a pedigree. In yet another embodiment, according to any of the other embodiments above, the at least one trait is latent and not phenotypically expressed in a member of a pedigree.

Strain JB-2, as JB 2-MS, has been deposited under the Budapest Treaty at the American Type Culture Collection (ATCC) in Manassas, Virginia, USA and has been assigned deposit number ATCC 76072. This strain was deposited in 1990, and transferred to the patent depository in Apr. 30, 1993. The deposited strain will be maintained in the depository for at least 30 years from the filing date of the application, or for the enforceable life of the patent, whichever is longer, and will be replaced if it ever becomes non-viable during that period. This strain will be irrevocably and without restriction released to the public upon the issuance of a patent.

Likewise, Strain JB-28 has been deposited under the Budapest Treaty with the Agricultural Research Service Culture Collection (NRRL) in Peoria, Illinois, and has been assigned deposit number 50407. This deposit was made on Jul. 13, 2010. The deposited strain will be maintained in the depository for at least 30 years from the filing date of the application, or for the enforceable life of the patent, whichever is longer, and will be replaced if it ever becomes non-viable during that period. This strain will be irrevocably and without restriction released to the public upon the issuance of a patent.

Other aspects of the invention may be achieved by providing hybrid *Agaricus bisporus* mushroom strains having a trait selected from the group consisting of sporelessness, reduced sporulation, incomplete development of spores, incomplete release of spores, and paler lamellae, incorporated therein. The traits are defined hereinabove. More particularly, the hybrid *Agaricus bisporus* mushrooms may be obtained by enabling fusion of a wild culture (or cultures descended or derived therefrom) capable of transmitting, and presumably incorporating genetic material determining, the trait(s) of non-sporulation, reduced sporulation, incomplete development of spores, incomplete release of spores, and/or paler lamellae, with at least a second culture. In one embodiment, the wild culture of *Agaricus bisporus* may be a wild tetrasporic strain. In another embodiment, the wild culture of *Agaricus bisporus* may be drawn from the class including cultures JB-2 and JB-28, and/or progeny descended or derived from any of the above cultures, with a second *Agaricus bisporus* culture, wherein mushrooms produced by the cultures of the invention have either an expressed trait and a sporeless phenotype, or a latent trait that is expressed in at least some of its descendents. In one embodiment, the hybrid strains do not use a homokaryon M1 as a direct and immediate progenitor.

In one or more embodiments, any of the hybrids strains above may be incorporated into materials selected from the group consisting of fresh or processed mushrooms, mushroom spores, mushroom spawn, mushroom preparations and extracts, mushroom inoculum, casing inoculum, casing soil, inoculated compost, colonized compost, and post-cropped compost. In other embodiments, any of the hybrid strains above can be subdivided into a component part selected from the vegetative mycelium, mycelial fragments, hyphal tips, spores, protoplasts, proteins, nucleic acids, cell wall matter, cytoplasm, and cellular constituents and extracts.

In another embodiment, the present invention further provides a method for obtaining viable recombinant homokaryotic or heterokaryotic offspring from a sporeless strain of a basidiomycete fungus comprising the step of induced cellular repartitioning of the contents of postmeiotic cells into vegetatively growing mycelial cultures. In one embodiment, the step of induced cellular repartitioning is achieved by a method of protoplast formation and regeneration. In another embodiment, the step of induced cellular repartitioning is achieved by mechanical reduction. In one embodiment, the postmeiotic cells are vegetative hyphae developed from explants of lamellar tissue. In another embodiment, the postmeiotic cells are basidia.

PREFERRED EMBODIMENT FOR CARRYING OUT THE INVENTION

Figure 1:
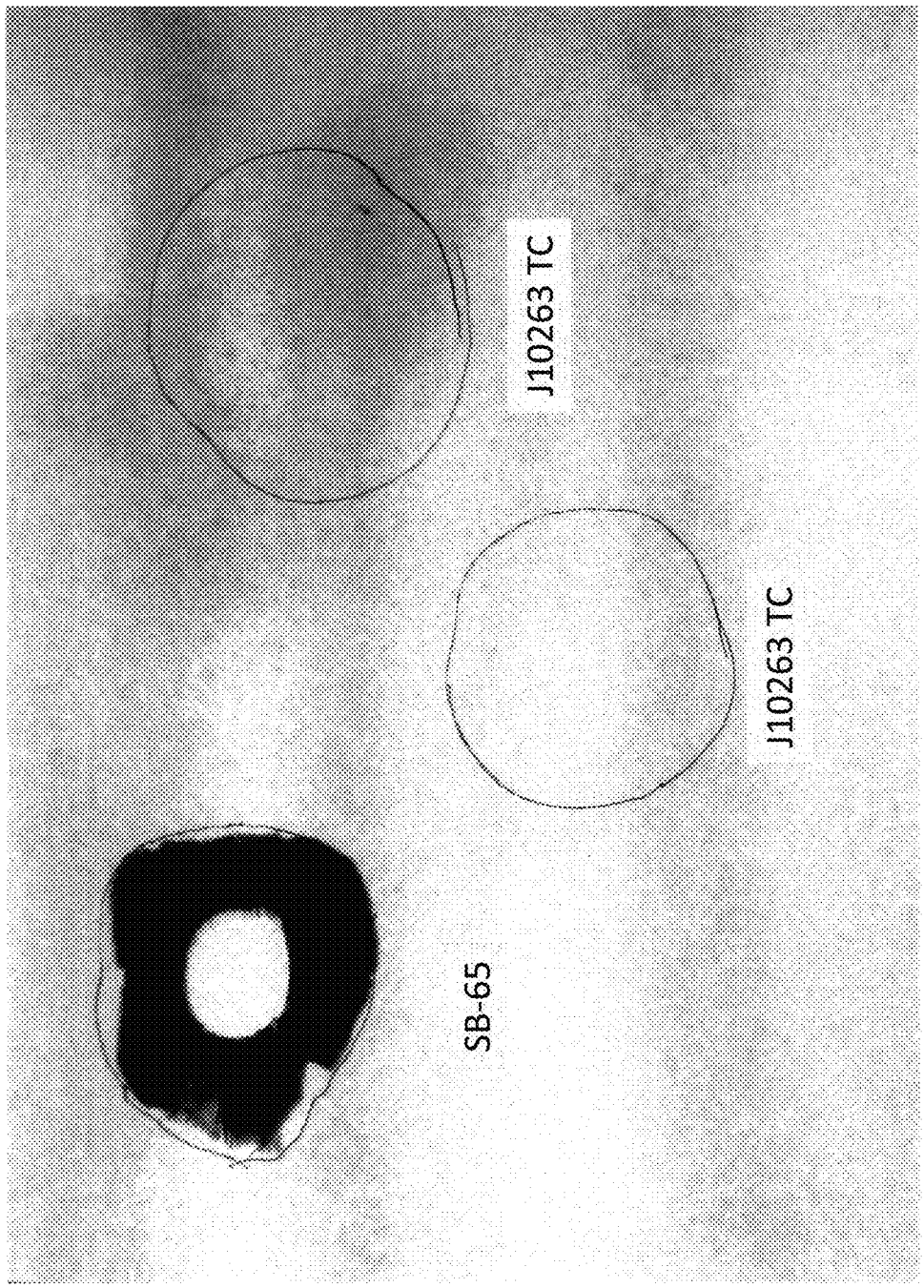
FIG. 1 is a photograph of a spore print experiment showing the comparison of the lack of sporulation ability between a mushroom of sporeless strain J10263 and the sporulation ability of a mushroom of the Sylvan control strain SB-65. In this example, the paper exhibits all spores released from each cap in an initial 23.5 hour period. Boundaries drawn in ink show the outline of each cap relative to the paper.

In the course of conducting Sylvan's proprietary breeding program on strains of *Agaricus bisporus* incorporating both new, wild germ plasm and established commercial germ plasm, an unexpected, serendipitous development was produced. The breeding stocks that were used all sporulate normally. It was surprisingly found, contrary to expectation and prediction, that these breeding stocks could confer a sporeless phenotype on offspring. It is known that most fusions between the bisporic taxonomic variety *bisporus* and the tetrasporic taxonomic variety *burnettii* produce typical, sporulating mushrooms. However, on rare occasions, an unprecedented absence of sporulation on the lamellae of mushrooms produced by some constructed strains of this intervarietal hybrid type was noted.

The first instances of non-sporulation in hybrid *Agaricus bisporus* mushroom offspring were observed in the proprietary Sylvan hybrids J250 and J258, which had, as one "homokaryon-parent," a homokaryon obtained from among spores of the first-generation proprietary Sylvan intervarietal hybrid J102, and, as a second "homokaryon-parent," a homokaryon from one of two commercial strains (WQ and S-381, respectively). J102 has the tetrasporic strain JB-2 as one parent and Sylvan's patented S600 hybrid strain for the other parent. As previously noted, JB-2 (as JB 2-MS) was deposited with the ATCC on 2 May 1990, where it received the designation ATCC 76072. It was converted by the ATCC to a deposit under the Budapest Treaty on 30 Apr. 1993 and will continue to be made publicly available under the Budapest Treaty for at least the effective life of any patent that issues herefrom.

To create these and other new hybrid strains, a container such as a petri dish containing a sterile microbiological medium, such as Potato Dextrose Agar (supplied by Difco), is asceptically inoculated first with a subclulture of one 'homokaryon parent', for example culture J102-s19 in the case of hybrid J250, followed by a second asceptic inoculation of a second 'homokaryon parent', culture WQ 9525 in this example, leaving the two inocula in close physical proximity. The two cultures are maintained in a clean incubator at 24 C, which allows hyphal growth away from the inoculation points. Conditions are maintained such that hyphae of the two haploid cultures grow into physical proximity with one another. At that point the process of anastomosis will initiate, involving the growth of compatible hyphae directly toward each other, and culminating in the physical contact and joining, or fusion, of pairs of compatible hyphae. As fusion progresses, the cell wall in the center of the contact zone is disassembled, exposing the two plasma membranes, which also fuse to open a cytoplasmic channel between the two hyphae. The establishment of the condition of cytoplasmic continuity is called plasmogamy, and results in the association of two sexually compatible haploid nuclei in a single hyphal cell. Hyphae that grow from that fusion cell will be populated by both of the nuclei, each donated by one of the two homokaryons, and thus heterokaryotic (n+n) growth of the new hybrid strain is established. This hybrid mycelium can then be transferred in subcultures taken from the fusion zone, to obtain a culture of the new hybrid strain.

The second set of instances of non-sporulation in hybrid mushroom offspring occurred in several proprietary Sylvan hybrids in which one or another of various homokaryons obtained from among spores of the first-generation intervarietal hybrid strain J453 was used as one "homokaryon-parent," and the commercially derived homokaryon M1 was the second "homokaryon-parent." J453 has the wild tetrasporic strain JB-28 as one parent and the commercial strain S-381 as the other parent. Homokaryotic culture J453-s7, a progenitor of Sylvan's sporeless strain J1901, has been deposited with the NRRL under the Budapest Treaty, and has been assigned deposit number NRRL 50406. This strain was deposited on Jul. 13, 2010. The deposited biological strains noted here will be maintained in the depository for at least 30 years, or for the effective life of the patent, whichever is longer, and will be replaced if necessary. This strain will be irrevocably and without restriction or condition released to the public upon the issuance of a patent. Hybrids in which non-sporulation was observed include J1901, J1902, J1906, J1923, and J1928; all of these produced white-capped mushrooms.

Mushrooms produced by both classes of hybrid strains were macro-anatomically normal and thus were 'true mushrooms'. Thus, it was expected that one would observe normal sporulation in them.

Sporeless mushroom strains in the latter class (i.e. hybrids between parents J453 and M1) were evaluated and found to be unsuitable for the commercial edible mushroom industry. One deficiency was a tendency to exhibit to an excessive degree, relative to white commercial control strains, discoloration after being handled. In the mushroom food industry this undesirable trait is called 'bruising'. However, one such crossed hybrid strain, J1901, was sufficiently promising that its suitability for other, non-food purposes was evaluated. In experiments unrelated to the assignee of record's strain crossbreeding program for developing novel hybrid edible mushrooms, it was determined that strain J1901 could be transformed with exogenous DNA from non-mushroom sources, and that exogenous non-mushroom genes could be expressed to produce heterologous proteins in strain J1901. The sporeless Agaricus strain J1901 was evaluated for this purpose because containment of genetically modified organisms is desirable and sometimes is required, and the absence of airborne spores makes containment simpler and more certain. This work on transformation using exogenous DNA was described in Velcko Jr. et al. (2004: Mush. Sci. 16: 591-597), the disclosure of which is incorporated herein by reference. Although J1901 is a true hybrid strain, being the result of a defined fusion between two homokaryons, the subsequently engineered transformed, genetically modified derivative strains are not the products of a further crossing process and therefore are not themselves novel hybrid strains.

Prior to the observations made in these two instances noted above, sporeless strains of Agaricus bisporus were unknown. In fact, given that all of the ancestral or parental wild and commercial strains represented in the above two pedigrees have sporulated normally, it was expected that any hybrid offspring developed would also all sporulate normally. The observation of sporelessness arising de novo in these cases suggests only that the sporeless trait observed in these two pedigrees may have a recessive character.

To investigate the heritability of the sporeless trait in further hybrids incorporating other strains, the homokaryon J453-s7 was fused with three homokaryons: 56B-4186, TS5-s4, and TS5-s19. All three of the resulting hybrids (called J10259, J10261, and J10263 respectively) produced brown-capped, macroanatomically typical, gilled, non-sporulating mushrooms. Three corresponding crosses of the commercial homokaryon U1-2 to the same three other homokaryons produced gilled, sporulating mushrooms. Thus J453-s7 is an example of a homokaryon of the present invention that can confer non-sporulation in the next generation, in at least some crosses including the examples studied to date.

To use these novel sporeless hybrids in extensions of the pedigrees into further generations, two obstacles had to be overcome. As noted above, without spore production, there is no source of naturally-occurring offspring from which to isolate recombined postmeiotic homokaryons. Further, research on Coprinopsis cinereus, another mushroom-forming basidiomycete fungus, had demonstrated that many mutations causing sporelessness act on the cell cycle by preventing meiosis from occurring or completing normally, preventing any genetic recombination from occurring at all. In such strains, not only the absence of spores, but also the absence of recombined postmeiotic nuclei, prevents the obtaining of sexually recombined offspring with novel genotypes that are required for the breeding of new and improved strains.

It could not be anticipated whether the sporeless strains had retained meiotic capability or not, nor whether the meiotic cycle would progress according to a time-schedule that would allow the generation of protoplasts containing single postmeiotic nuclei. Nonetheless, a method was developed and investigated for obtaining such postmeiotic offspring, including homokaryons and heterokaryons, by enzymatically making and regenerating protoplasts from hypothetically post-meiotic cells from axenic lamellae of non-sporulating A. bisporus mushrooms. To carry out our method, essentially as taught by Kerrigan et al., Mycologia 84: 575-579 (1992), applied to lamellae rather than hyphae, a buffer containing an osmiticum such as 0.6M sucrose is prepared and sterilized, and to this an effective amount of a cell-wall-digesting enzyme such as (at that time) Novozyme 234 (Novo Labs) is added. To aliquots of this solution in small tubes, for example 1.5 ml microcentrifuge tubes, pieces of lamellae, about 3-5 mm$^2$, aseptically removed from lamellae still covered by the veil, from mushrooms of a sporeless strain such as J10263, are added. Lamellae are used because they contain the only type of postmeiotic cells, the basidia, that occur in sporeless strains. Incubation is carried out at a temperature specific to the enzyme preparation for a sufficient time interval, for example at room temperature for ca. 60 minutes. The protoplasts (=small 'repartitioned' cytoplasmic subunits bounded by plasma membranes), released from the enzymatically perforated hyphae and suspended in the buffer, are gently filtered away, through glass wool and fine mesh nylon cloth, from the lamellar cell wall debris, and are collected by gentle centrifugation in small tubes, then are separated from the active enzyme by the pipetting away of the overlying enzyme solution, are resuspended in more buffer solution, and are gently, aseptically transferred to osmotically stabilized solid nutrient media such as PDA+0.6M sucrose in petri plates. The protoplasts are maintained in a clean incubator at 24 C for several days until they begin to regenerate cell walls and resume hyphal growth. Individual regenerant colonies are aseptically isolated and individually propagated for analysis and characterization, for example by fertility (cultivation) testing (to identify homokaryons), and by molecular fingerprinting using co-dominant markers (to identify postmeiotic, recombined genotypes).

This method was applied to the non-sporulating hybrid brown Sylvan strains J10259 and J10263. Strain J10263 has been deposited under the Budapest Treaty with the NRRL, and has been assigned deposit number NRRL 50408. The deposit was made on Jul. 13, 2010. It, too, will be maintained in the depository for at least 30 years, or for the effective life of the patent, whichever is longer, and will be replaced if necessary. This strain will be irrevocably and without restriction or condition released to the public upon the issuance of a patent.

Success has been had in obtaining protoplasts from sporeless mushrooms produced by strains J10263 and J10259, and regenerating them axenically into pure cultures. Using multiple molecular markers, genetic fingerprints of the protoplast-regenerant cultures were developed and individual homokaryotic and heterokaryotic cultures were discovered with recombined genotypes that had re-assorted the parental alleles during meiosis, as shown in Tables 1 and 2 below.

TABLE 1

Genotypes of seven postmeiotic homokaryotic offspring of Sylvan hybrid J10263

| Marker: | Protoplast Regenerant No. | | | | | | | J453-s7 | TS5-s19 |
|---|---|---|---|---|---|---|---|---|---|
| | 1 | 2 | 8 | 14 | 28 | 29 | 30 | | |
| PR6-HaeIII | A | A | A | A | A | A | A | A | [B] |
| p33n5-P | B | B | B | A | A | B | A | A | [B] |
| PR2-HaeIII | A | A | A | A | B | B | B | A | [B] |

Table 1 shows the 3-locus genotypes of seven homokaryotic cultures obtained from regenerated protoplasts of lamellae from sporeless mushrooms produced by Sylvan hybrid strain J10263. Protoplasts were prepared and regenerated as described above. A and B are arbitrarily named and assigned alleles at the three marker loci. The markers are all in the public domain and are used regularly by practitioners of the art. Markers PR2 and PR6 were first taught by Callac et al., FEMS Microbiol. Lett. 146: 235-240 (1997). Marker P33n5-P is a PCR-amplicon version of the RFLP marker called p33n5 taught by Kerrigan et al., Genetics 133: 225-236 (1993), and is sometimes also called PR-12 (P. Callac, pers. comm.). The genotypes of the "parental homokaryons" (of J10263) J453-s7 (=AAA) and TS5-s19 (=BBB, inferred) are shown at right.

The number of possible genotypes at three unlinked markers among postmeiotic nuclei and homokaryons is eight (=two to the third power; note that some linkage between PR2 and PR6 has been documented (Callac et al. 1997), which means that four of the eight possible resulting genotypes are expected to be relatively more rare). The two "homokaryon-parental" genotypes (AAA, BBB) should in the simplest case each be present among one-eighth (12.5%) of the recombined postmeiotic nuclei and homokaryons, but they cannot be distinguished from the premeiotic nuclei based on only three markers. Protoplast regenerant No. 14 is an example of one of these two genotypes (AAA). However, significantly, among the remaining six protoplast regenerants, three different, new, meiotically recombined haploid genotypes were recovered in this experiment: ABA in Nos. 1, 2, and 8, AAB in Nos. 28 and 30, and ABB in No. 29. Thus in this small sample of seven homokaryons regenerated from protoplasted sporeless lamellae, four genotypes were obtained, three of which did not match either of the two 'parental homokaryon' genotypes. This demonstrates that meiotic recombination had occurred prior to the protoplasting process, and that protoplasting repartitioned the four postmeiotic nuclei of the basidial cells into viable new compartments containing fewer nuclei, most likely one, haploid nucleus. Thus our method provides for postmeiotic homokaryotic offspring from sporeless mushrooms. Although Table 1 does not show data on recombinant heterokaryotic offspring, several of these were also obtained among the protoplast regenerants of this experiment. This technique, applied to nonsporulating strains including those described hereinabove, overcomes two of the greatest obstacles to the breeding of sporeless strains. Homokaryotic strains obtained as disclosed hereinabove have been used in further crosses to diverse other strains.

TABLE 2

Genotypes of four postmeiotic offspring of Sylvan hybrid J10259

| Marker: | Protoplast Regenerant No. | | | | J453-s7 | 56B-4186 |
|---|---|---|---|---|---|---|
| | 2 | 3 | 5 | 6 | | |
| PR6-HaeIII | C | C | A | H | A | C |
| PR7-RsaI | H | A | H | C | A | C |

Table 2 shows the 2-locus genotypes of four homokaryotic cultures obtained from regenerated protoplasts of lamellae from sporeless mushrooms produced by Sylvan hybrid strain J10259. Protoplasts were prepared and regenerated as described above. A and C are arbitrarily named and assigned alleles at the two marker loci. H designates the heteroallelic phenotype of A+C, present in J10259. The markers are all in the public domain and are used regularly by practitioners of the art. Markers PR6 and PR7 were first taught by Callac et al., FEMS Microbiol. Lett. 146: 235-240 (1997). The genotypes of the "parental homokaryons" (of J10263) J453-s7 (=AAA) and 56B-4186 (=CCC) are shown at right. Regnerant No. 3 has a homoallelic genotype consistent with it being a homokaryon, and it is a non-parental, therefore a recombined postmeiotic, homokaryon. Regenerants Nos. 2, 5, and 6 are each heteroallelic at one of the marker loci, but homoallelic at the other locus, and each of the three is unique. They represent recombined heterokaryotic offspring which are also useful in selection methods for *Agaricus bisporus* strain improvement, for example in single-spore isolate (=SSI) selection approaches.

Investigations on the expression of the sporeless trait were conducted on several sporeless hybrids produced according to the methods disclosed above. To make observations, a lamella was excised and laid flat on a glass microscope slide to make a 'dry mount' with no cover slip. Using a compound optical microscope with objective lenses of 20× or 25× magnification, basidial apices could be observed. In sporulating strains, sterigmata and spores at various stages of development could be observed on basidial apices. In "sporeless" strains as defined herein, normal spore development could not be observed. Instead, a range of "sporeless" trait expression was observed. In some hybrids, little or no development of sterigmata or spore-initials at the apex of the basidium was observed. In other hybrids, a limited degree of spore-development was observed; however the spores were tiny, not completely developed, and were not released from the basidia as normal spores would be. Sporulation in gilled mushrooms is defined by both the (normal, meaning characteristic and viable) development and the successful release of spores from the basidium into the air. It was hypothesized that the specific genetic background of each of the two partners in the hybrid determines the precise degree of expression of the sporeless trait.

Figure 2:
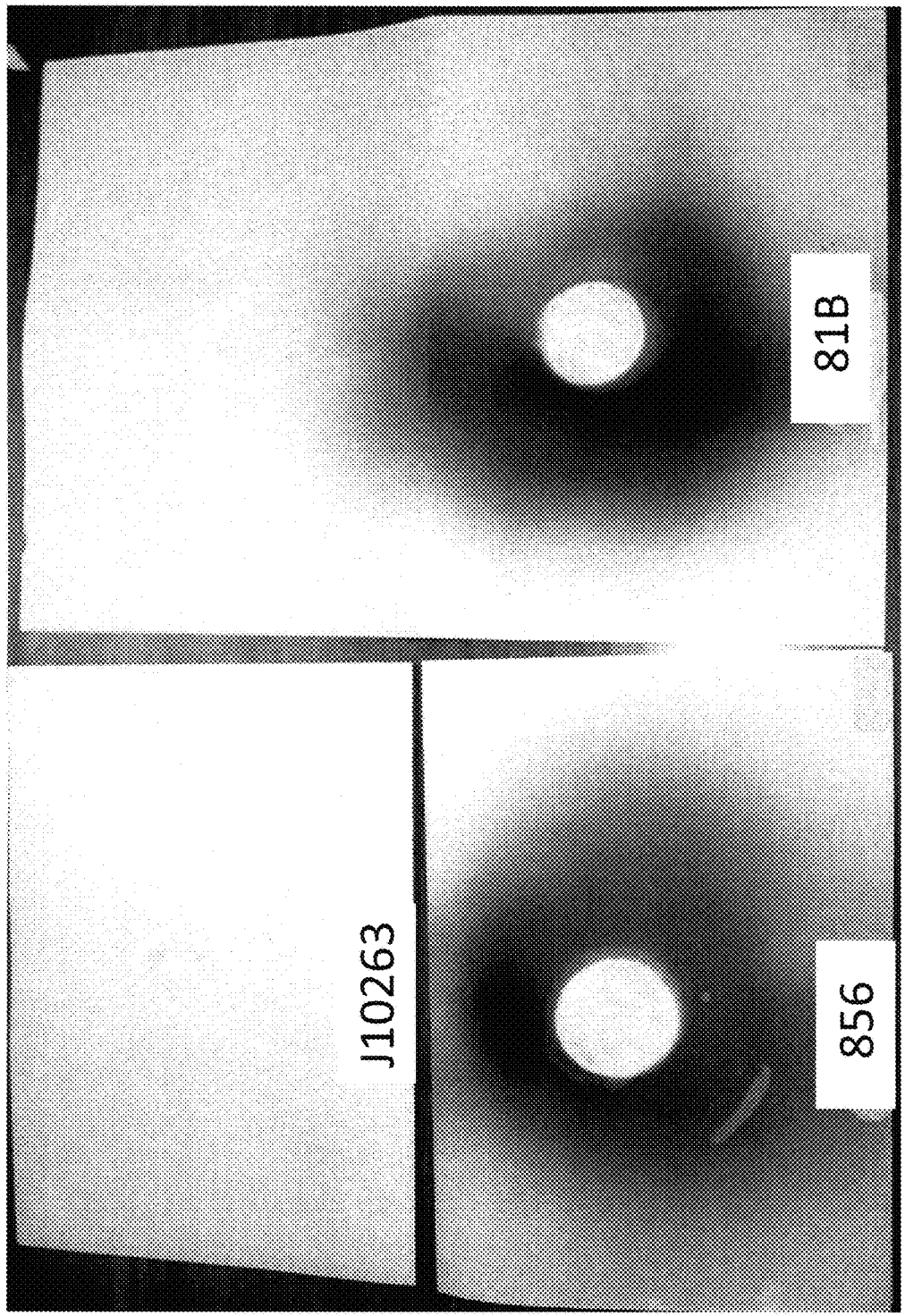
FIG. 2 is a photograph of a spore print experiment showing the comparison of the lack of sporulation ability between a mushroom of sporeless strain J10263 and the sporulation ability of a mushroom of the Sylvan commercial control strains 856 and 81B. The sampling interval for sporulation was approximately 24 hours.

It has been confirmed in numerous experiments that the sporeless hybrids we have produced do not produce a detectable spore deposit. To do this, fresh J10263 mushroom cap samples at days 1, 2, 3, 4, and 5 after velar rupture were suspended over white paper, without contacting the paper. A plastic cover allowing slight ventilation while blocking most air currents was placed over the mushroom cap and paper. Control SB-65 mushrooms sporulated normally, and the dark brown spores were easily observed on the white paper. No spore deposit could be observed from the non-sporulating mushrooms at any stage of development. This was repeated at weekly intervals in three successive "flushes" of mushrooms from a single crop. Examples of the results on the sporeless strain J10263 in comparison with the control strain SB-65 mushrooms are shown in FIG. 1. and FIG. 2. Similar results from simplified versions of the above experiment on sporeless strains J1901 and J10259 also produced no visible spore print on white paper. These results are confirmatory of the sporeless condition that we have observed under the microscope for diverse strains from these pedigrees.

Thus, the successful application of a practical method for developing non-sporulating strains of *Agaricus bisporus* mushrooms by employing wild germ plasm capable of conferring a trait of sporelessness upon offspring, presumably by incorporating genetic material specifically determining the trait of sporelessness, has been demonstrated. It has been shown that both white-capped and brown-capped non-sporulating mushrooms can be produced according to this method. It has been further demonstrated that an additional method for obtaining recombinant postmeiotic homokaryotic offspring from non-sporulating *Agaricus* mushrooms has been developed, and that successful next-generation crosses can be obtained using those homokaryons as parents in further crosses. The latter method can be employed in the obtaining of recombinant homokaryotic offspring from sporeless basidiomata of other genera, and potentially all genera, of basidiomycetes producing fleshy basidiomata, including gilled mushrooms.

Thus, hybrids strains produced by the methods disclosed herein, or belonging to this class but produced by other means or methods, are claimed. It is to be understood that any variations evident fall within the scope of the claimed invention and thus, the selection of specific hybridization techniques and sources of homokaryons and heterokaryons can be determined without departing from the spirit of the invention herein disclosed and described. Further, it will be understood that the scope of the invention is not necessarily limited to methods that produce mushrooms strains or cultures that are sporeless, but rather to those strains or cultures that are produced from cultures having at least one parent or lineage or derivative that is sporeless. Thus, the scope of the invention shall include all modifications and variations that may fall within the scope of the attached claims.

What is claimed is:

1. A method for producing a hybrid mushroom strain of *Agaricus bisporus* and determining that an *Agaricus bisporus* culture carries a genetic determinant for at least one sporeless trait selected from the group consisting of non-sporulation, reduced sporulation, incomplete development of spores, incomplete release of spores, and paler lamellae, the method comprising:
   placing a first culture of *Agaricus bisporus* and a second culture of *Agaricus bisporus* in close proximity on a suitable sterile culture medium, wherein said step of placing enables fusion via anastomosis and plasmogamy between the first culture of *Agaricus bisporus* and the second culture of *Agaricus bisporus*, wherein the first culture is a homokaryoni an aneuploid, or a karyotypically indeterminate culture that has been identified to be germ plasm capable of transmitting to the offspring at least one sporeless trait, to produce the hybrid mushroom strain of *Agaricus bisporus*;
   wherein when the hybrid strain obtained from said fusion has an expressed trait for a sporeless phenotype, the second culture is determined to carry a genetic determinant for at least one sporeless trait; and
   wherein said method does not use any genetic marker or MAS technique to mark alleles of any gene hypothetically associated with the production of a sporeless phenotype in mushrooms of *Agaricus bisporus*.

2. The method according to claim 1, wherein a new hybrid *Agaricus* mushroom strain is produced, the method comprising:
   selecting the culture that has been determined to carry the genetic determinant for the at least one sporeless trait; and
   carrying out hybridization between a third culture of *Agaricus bisporus* and the selected culture, said step of carrying out hybridization including a step of placing the two cultures in close proximity on a suitable sterile culture medium, wherein said step enables fusion via anastomosis and plasmogamy between the two cultures, thereby producing the new hybrid *Agaricus* mushroom strain, and wherein the selected culture is selected from the group consisting of homokaryons, aneuploidy, or karyotypically indeterminate cultures.

3. A method for obtaining viable recombinant postmeiotic homokaryotic or heterokaryotic offspring from a sporeless strain of a basidiomycete fungus comprising:
   selecting basidiomata from a sporeless strain of a basidiomycete fungus at a stage of development in which meiosis has occurred in some basidia; axenically excising lamellae from said basidiomata;
   applying a technique for repartitioning of contents of postmeiotic cells of said lamellae into vegetatively growing mycelial cultures, said technique being selected from
   (a) enzymatically making and regenerating protoplasts from the excised lamellae, or
   (b) mechanically reducing the post-meiotic cells by performing (i) microsurgery or (ii) laser surgery to sever hyphal tips or fragment mycelia;
   wherein the postmeotic cells are basidia, or are vegetative hyphae developed from basidia among explants of lamellar tissue.

* * * * *